(12) United States Patent  
Schnaubelt et al.

(10) Patent No.: US 8,629,146 B2
(45) Date of Patent: Jan. 14, 2014

(54) METHOD FOR STEREOSELECTIVE SYNTHESIS OF BICYCLIC HETEROCYCLIC COMPOUNDS

(71) Applicants: Juergen Schnaubelt, Oberhoefen/Warthausen (DE); Wenjun Tang, Southbury, CT (US)

(72) Inventors: Juergen Schnaubelt, Oberhoefen/Warthausen (DE); Wenjun Tang, Southbury, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 13/761,211

(22) Filed: Feb. 7, 2013

(65) Prior Publication Data

US 2013/0211081 A1   Aug. 15, 2013

(30) Foreign Application Priority Data

Feb. 9, 2012   (EP) .................................. 12154688

(51) Int. Cl.
*A61K 31/497* (2006.01)
*C07D 237/00* (2006.01)

(52) U.S. Cl.
USPC ....................... 514/252.1; 544/231

(58) Field of Classification Search
None
See application file for complete search history.

(56) References Cited

U.S. PATENT DOCUMENTS

| | | | |
|---|---|---|---|
| 6,924,285 B2 | 8/2005 | Hummelsbach et al. | |
| 7,119,084 B2 | 10/2006 | Hummelsbach et al. | |
| 7,910,731 B2 | 3/2011 | Hummelsbach et al. | |
| 8,343,982 B2 | 1/2013 | Hummelsbach et al. | |
| 2004/0048880 A1 | 3/2004 | Himmelsbach et al. | |
| 2005/0182043 A1 | 8/2005 | Himmelsbach et al. | |
| 2006/0270672 A1 | 11/2006 | Himmelsbach et al. | |
| 2007/0135463 A1 | 6/2007 | Himmelsbach et al. | |
| 2009/0036676 A1 | 2/2009 | Himmelsbach et al. | |
| 2011/0046148 A1 | 2/2011 | Himmelsbach et al. | |
| 2011/0077246 A1 | 3/2011 | Himmelsbach et al. | |
| 2011/0183987 A1 | 7/2011 | Ostermeier et al. | |
| 2013/0030003 A1 | 1/2013 | Pfrengle et al. | |

FOREIGN PATENT DOCUMENTS

| | | | |
|---|---|---|---|
| WO | 03082290 A1 | 10/2003 | |
| WO | 2007068552 A1 | 6/2007 | |
| WO | 2009098061 A1 | 8/2009 | |
| WO | 2011015526 A1 | 2/2011 | |
| WO | WO 2011015526 A1 * | 2/2011 | |
| WO | 2012104206 A1 | 8/2012 | |

* cited by examiner

*Primary Examiner* — James O Wilson
*Assistant Examiner* — Oluwafemi Masha
(74) *Attorney, Agent, or Firm* — Michael P. Morris; Edward S. Lazer

(57) ABSTRACT

The invention relates to a method for the stereoselective preparation of a compound of formula (5), optionally in the form of the tautomers thereof,

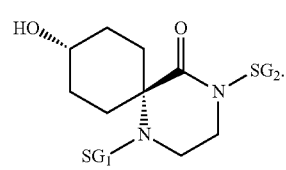

(5)

7 Claims, No Drawings

METHOD FOR STEREOSELECTIVE SYNTHESIS OF BICYCLIC HETEROCYCLIC COMPOUNDS

The invention relates to a method for the stereoselective preparation of a compound of formula (5), optionally in the form of the tautomers thereof,

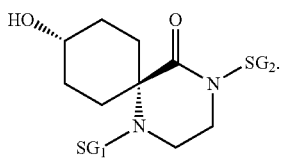
(5)

BACKGROUND OF THE INVENTION

Compounds of formula (5), optionally in the form of the tautomers thereof, are valuable intermediates in methods for the stereoselective preparation of the compound of formula (I), optionally in the form of the tautomers thereof, and optionally the pharmacologically acceptable acid addition salts thereof,

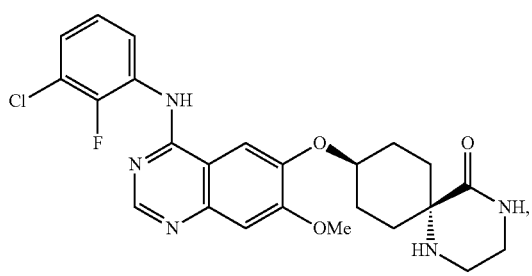
(I)

which compound has valuable pharmacological properties, particularly an inhibiting action on signal transduction mediated by tyrosine kinases, and for the treatment of diseases, particularly tumoral diseases, benign prostatic hyperplasia and diseases of the lungs and respiratory tract.

Quinazoline derivatives are known from the prior art as active substances for example for the treatment of tumoral diseases and also diseases of the lungs and airways. Methods for preparing quinazoline derivatives are described in WO2003082290 and WO2007068552. WO2009098061 and WO2011015526 disclose methods of preparing the compound (I).

The problem of the present invention is to provide an alternative stereoselective synthesis process for preparing the compound of formula (I) or an advantageous method of preparing important intermediates of this synthesis.

DETAILED DESCRIPTION OF THE INVENTION

The present invention solves the problem stated above by means of the method of synthesis described hereinafter.

The invention relates to a process for the stereoselective preparation of the compound of formula (5), optionally in the form of the tautomers thereof,

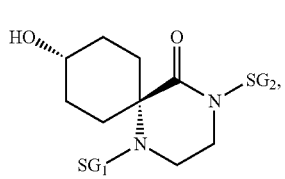
(5)

wherein
$SG_1$ denotes a protective group selected from among trifluoroacetyl, acetyl, benzoyl and pivaloyl,
$SG_2$ denotes a protective group selected from among tert.-butoxycarbonyl, ethoxycarbonyl and methoxycarbonyl,
characterized in that the process comprises reaction steps (C) and (D), where
(C) is the reaction of the compound of formula (3)

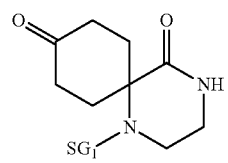
(3)

to form a compound of formula (4)

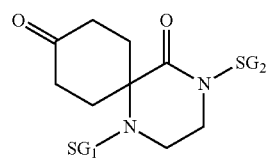
(4)

and
(D) is the reduction of the compound of formula (4) to form a compound of formula (5),
wherein process steps (C) and (D) are carried out successively in the order stated.
In a preferred process the reaction steps (C) and (D) are preceded by further reaction steps (A) and (B),
where
(A) denotes the reaction of the compound of formula (1)

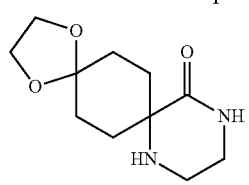
(1)

to form a compound of formula (2)

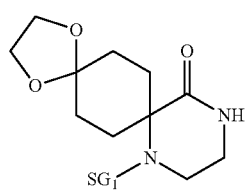
(2)

and (B) denotes the reaction of the compound of formula (2) to form a compound of formula (3)

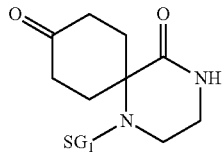
(3)

while process steps (A), (B), (C) and (D) are carried out successively in the order stated.

Also preferred is a process for the stereoselective preparation of the compound of formula (5), optionally in the form of the tautomers thereof,

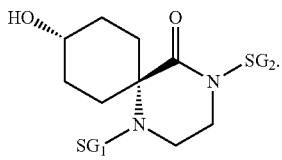
(5)

characterized in that

SG$_1$ denotes trifluoroacetyl, and

SG$_2$ denotes tert-butoxycarbonyl.

The invention further relates to an intermediate of formula (2), optionally in the form of the tautomers or salts thereof,

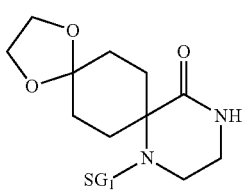
(2)

wherein,

SG$_1$ denotes a protective group selected from among trifluoroacetyl, acetyl, benzoyl and pivaloyl.

Preferred is an intermediate of formula (2A), optionally in the form of the tautomers or salts thereof,

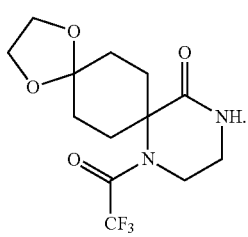
(2A)

The invention further relates to an intermediate of formula (4), optionally in the form of the tautomers or salts thereof

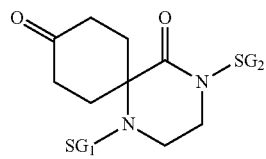
(4A)

wherein

SG$_1$ denotes a protective group selected from among trifluoroacetyl, acetyl, benzoyl and pivaloyl, and SG$_2$ denotes a protective group selected from among tert-butoxycarbonyl, ethoxycarbonyl and methoxycarbonyl.

Preferred is an intermediate of formula (4A), optionally in the form of the tautomers or salts thereof,

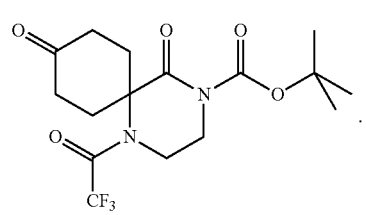
(4A)

The invention further relates to the use of the intermediates of formula (2) or (4), preferably the intermediates (2A) or (4A), optionally in the form of the tautomers or salts thereof, for preparing a compound of formula (I), optionally in the form of the tautomers or salts thereof,

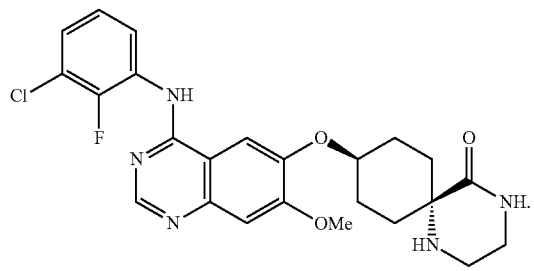
(I)

The novel use of the intermediates (2) or (4), preferably of the intermediates (2A) or (4A), for preparing a compound of formula (I) may be carried out via the preparation of the compound of formula (5) and the subsequent synthesis steps (G) to (L) described in WO2012104206.

Compared with the synthesis described in WO2012104206 the following advantages are obtained, particularly with a view to the large-scale industrial production of the compound (I):

a) The total yield of compound (5) starting from compound (I) is significantly increased by between 10 to 20%, for example by 15%, to 60%.

b) Smaller amounts of acetic acid are used for the acetal splitting and the resultant larger quantities of acid waste are avoided.

c) The use of sodium borohydride is avoided by using a less expensive heterogeneously catalytic hydrogenation process.

In process steps (A), (B), (C), (D) alternative reagents, catalysts and solvents may be used, preferably selected from among the reagents, catalysts and solvents listed in Table I.1 to I.4:

TABLE I.1

Alternative solvent

| process step | Solvent | particularly preferred solvent |
|---|---|---|
| (A) | Me—THF, THF, toluene, DMF, NMP, ethyl acetate, methyl-cyclohexane, cyclohexane, $CH_2Cl_2$ and dioxane | Me—THF and methyl-cyclohexane |
| (B) | water, methanol, ethanol, isopropanol and dioxane | water and methanol |
| (C) | Me—THF, THF, DMF, NMP, acetone, acetonitrile and dioxane | acetonitrile |
| (D) | methanol, ethanol, isopropanol, water and ethyl acetate | ethanol |

TABLE I.2

Alternative bases and acids

| process step | | bases or acids | particularly preferred bases or acids |
|---|---|---|---|
| (A) | bases | N-methylmorpholine, triethylamine, N-ethyldiisopropylamine (Hünig base), N-methylpyrrolidine and N-methylpiperidine | N-methylmorpholine |
| (B) | acids | acetic acid, trifluoroacetic acid, hydrochloric acid, sulphuric acid, methanesulphonic acid and p-toluenesulphonic acid | acetic acid |

TABLE I.3

Alternative reagents

| process step | Reagents | particularly preferred reagents |
|---|---|---|
| (A) | trifluoroacetic anhydride, methyl trifluoroacetate, trifluoroacetyl chloride and trifluoroacetylimidazole | trifluoroacetic anhydride |
| (C) | di-tert-butyldicarbonate | di-tert-butyldicarbonate |

TABLE I.4

Alternative catalysts

| process step | Catalysts | particularly preferred catalysts |
|---|---|---|
| (C) | dimethylaminopyridine (DMAP) and pyridine | DMAP |
| (D) | Raney nickel, platinum/charcoal, platinum dioxide, ruthenium/charcoal and rhodium/charcoal | Raney nickel |

The process steps (A) to (D) described above are preferably carried out in the following temperature ranges:
In process step:
(A): preferably 0 to 70° C., particularly preferably 10 to 20° C.;
(B): preferably 20 to 70° C., particularly preferably 60 to 70° C.;
(C): preferably 0 to 78° C., particularly preferably 10 to 30° C.;
(D): preferably 20 to 80° C., particularly preferably 40 to 70° C.

Scheme 1 illustrates the synthesis according to the invention. All the compounds are shown in the form of their bases.

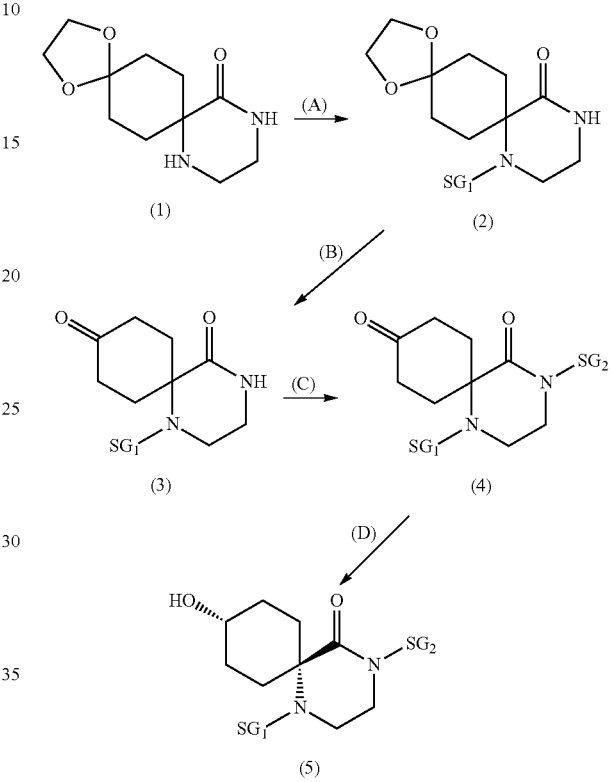

In process step (A), intermediate (1) is protected at the amine nitrogen using 2.0 to 3.0 molar equivalents of reagent in the presence of 2.2 to 3.2 molar equivalents of base. In process step (B), the ketal (2) is deprotected under aqueous acidic conditions, using 2.0 to 4.0 molar equivalents of acid, to obtain the corresponding ketone (3). In the next step (C) the amide nitrogen that is still free is protected with 1.0 to 1.5 molar equivalents of reagent in the presence of 2 to 10 molar percent of catalyst. In the last step (D) catalytic stereoselective reduction of the keto group with hydrogen takes place to form the cis-configured alcohol (5).

In a preferred embodiment, in process step (A) intermediate (1) is protected at the amine nitrogen using 2.2 molar equivalents trifluoroacetic anhydride (TFAA) in the presence of 2.4 molar equivalents N-methylmorpholine (NMM) trifluoroacetyl. Process step (B) describes the aqueous acidic deprotection of the ketal (2) to form the corresponding ketone (3) using 2.8 molar equivalents acetic acid (HOAC). In the next step (C) the amide nitrogen that is still free is protected by treating with 1.2 molar equivalents of di-tert-butyldicarbonate in the presence of 5 molar percent of dimethylaminopyridine to form a carbamate. In the last step (D) catalytic stereoselective reduction of the keto group is carried out with hydrogen to obtain the cis-configured alcohol (5).

The following Examples serve to illustrate the processes carried out by way of example for preparing the compound of formula (5). These Examples are intended as an illustration of the invention without restricting it to their content.

EXAMPLE 1

1,4-Dioxa-9-(2,2,2-trifluoro-acetyl)-9,12-diaza-dispiro[4.2.5.2]pentadecan-13-one

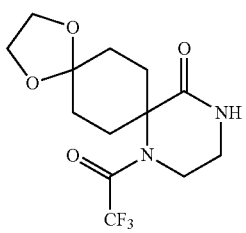

(2A)

Process Step (A)

107.2 g of N-methylmorpholine are added dropwise to 100 g 1,4-dioxa-9,12-diaza-dispiro[4.2.5.2]pentadecan-13-one in 300 ml of 2-methyltetrahydrofuran at ambient temperature (RT corresponds to 20 to 25° C.). Then the mixture is cooled to 6-10° C. and 204.2 g of trifluoroacetic anhydride are added dropwise. During this addition the temperature rises to RT. After 120 min, 200 ml of water and 450 ml of methylcyclohexane are added successively. After 60 min the suspension is cooled to 0° C. After 25 min the precipitate is filtered off and washed successively with 100 ml of water and 100 ml methylcyclohexane. After drying at 50° C. in vacuo, 137.9 g of product is obtained.

Mass spectrum (ESI+): m/z=323 [M+H]$^+$
M.p. 224.8° C.

EXAMPLE 2

1-(2,2,2-trifluoro-acetyl)-1,4-diaza-spiro[5.5]undecane-5,9-dione

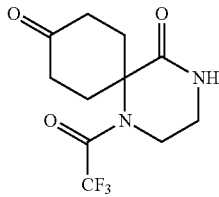

(3A)

Process Step (B)

195 ml of water and 65 ml of acetic acid are added to 130 g of 1,4-dioxa-9-(2,2,2-trifluoro-acetyl)-9,12-diaza-dispiro[4.2.5.2]pentadecan-13-one in 390 ml of methanol. The mixture is heated to 68° C. and stirred for 120 min at this temperature. Then 325 ml of solvent are distilled off. The resulting suspension is cooled to 5° C. After 30 min the precipitate is filtered off and the residue is washed with 50 ml of tert.-butylmethylether. After drying at 50° C. in vacuo, 101.4 g of product is obtained.

Mass spectrum (ESI+): m/z=279 [M+H]$^+$
M.p. 169.0° C.

EXAMPLE 3

Tert-butyl 5,9-dioxo-1-(2,2,2-trifluoro-acetyl)-1,4-diaza-spiro[5.5]undecane-4-carboxylate

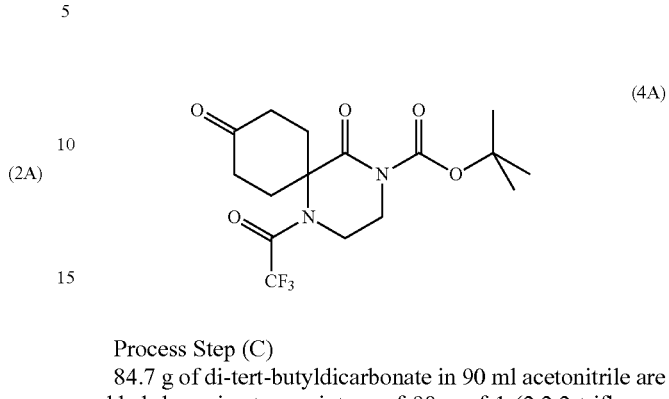

(4A)

Process Step (C)

84.7 g of di-tert-butyldicarbonate in 90 ml acetonitrile are added dropwise to a mixture of 90 g of 1-(2,2,2-trifluoro-acetyl)-1,4-diaza-spiro[5.5]undecane-5,9-dione and 1.98 g of dimethylaminopyridine in 180 ml of acetonitrile at RT within 75 min. After 60 min 990 ml of water are added and seeded. After 60 min the precipitate is filtered off and washed with 180 ml of water. After drying at 50° C. in vacuo 113.8 g of product is obtained.

Mass spectrum (ESI$^+$): m/z=379 [M+H]$^+$
M.p. 114.9° C.

EXAMPLE 4

Tert-butyl(cis)-9-hydroxy-5-oxo-1-(2,2,2-trifluoro-acetyl)-1,4-diaza-spiro[5.5]undecane-4-carboxylate

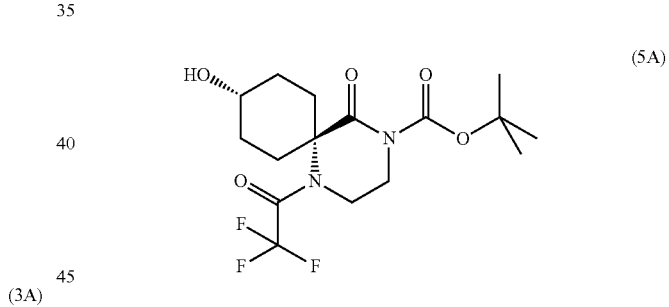

(5A)

Process Step (D)

5.1 g of Raney nickel are added to 17 g of tert-butyl 5,9-dioxo-1-(2,2,2-trifluoro-acetyl)-1,4-diaza-spiro[5.5]undecane-4-carboxylate in 170 ml of ethanol. The reaction mixture is hydrogenated in the autoclave for 10 hours at 60° C. and 50 bar hydrogen pressure. Then the catalyst is filtered off and the filter cake is washed with 40 ml of ethanol. 165 ml of ethanol are distilled off. 374 ml of toluene are added to the residue and a further 136 ml of solvent are distilled off. The resulting solution is combined with 55 ml of water at 60° C. and the phases are separated. A further 195 ml of solvent are distilled off from the organic phase remaining. The resulting suspension is cooled to 2° C. within 120 min. After 30 min the precipitate is filtered off and washed twice with 20 ml of toluene. After drying at 50° C. in vacuo, 12.6 g of product is obtained, which still contains approx. 6% of trans-product.

Mass spectrum (ESI$^+$): m/z=381 [M+H]$^+$
M.p. 163.0° C.

Compilation of Data

A Waters mass spectrometer ZQ 2000 (Electrospray source) is used to compile the MS data shown.

The invention claimed is:

1. A method for the stereoselective preparation of the compound of formula (5), optionally in the form of the tautomers thereof,

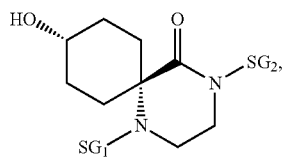

wherein

SG$_1$ denotes a protective group selected from among trifluoroacetyl, acetyl, benzoyl and pivaloyl, SG$_2$ denotes a protective group selected from among tert.-butoxycarbonyl, ethoxycarbonyl and methoxycarbonyl, characterized in that the method comprises reaction steps (C) and (D), where (C) is the reaction of the compound of formula (3)

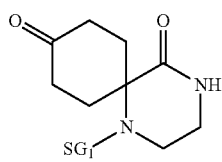

to form a compound of formula (4)

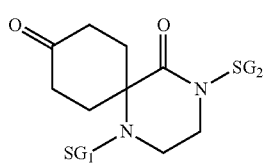

and (D) is the reduction of the compound of formula (4) to form a compound of formula (5), wherein process steps (C) and (D) are carried out successively in the order stated.

2. The method according to claim 1, characterized in that reaction steps (C) and (D) are preceded by further reaction steps (A) and (B), wherein (A) denotes the reaction of the compound of formula (1)

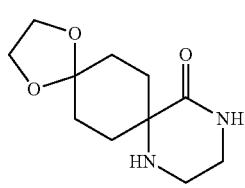

to form a compound of formula (2)

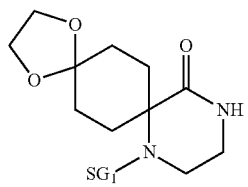

and (B) denotes the reaction of the compound of formula (2) to form a compound of formula (3)

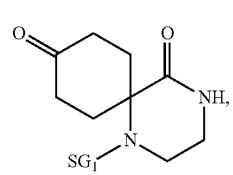

wherein process steps (A), (B), (C) and (D) are carried out successively in the order stated.

3. The method according to claim 1 for the stereoselective preparation of the compound of formula (5A), optionally in the form of the tautomers thereof,

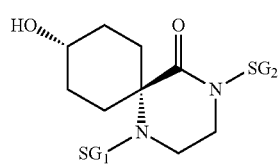

characterized in that

SG$_1$ denotes trifluoroacetyl, and

SG$_2$ denotes tert-butoxycarbonyl.

4. The intermediate of formula (2) according to claim 2, optionally in the form of the tautomers or salts thereof

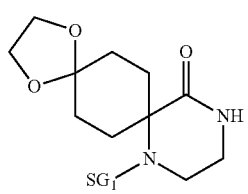

wherein

SG$_1$ denotes a protective group selected from among trifluoroacetyl, acetyl, benzoyl and pivaloyl.

5. The intermediate of formula (2A) according to claim 4, optionally in the form of the tautomers or salts thereof,

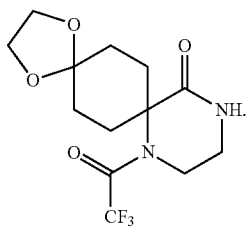

(2A)

6. The intermediate of formula (4) according to claim 1, optionally in the form of the tautomers or salts thereof,

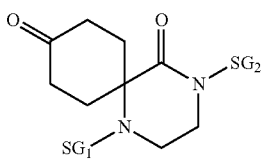

(4)

wherein
- SG$_1$ denotes a protective group selected from among trifluoroacetyl, acetyl, benzoyl and pivaloyl, and
- SG$_2$ denotes a protective group selected from among tert.-butoxycarbonyl, ethoxycarbonyl and methoxycarbonyl.

7. The intermediate of formula (4A) according to claim 6, optionally in the form of the tautomers or salts thereof

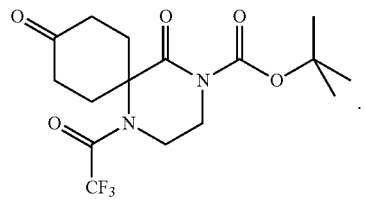

(4A)

* * * * *